(12) United States Patent
Gerber et al.

(10) Patent No.: US 7,226,483 B2
(45) Date of Patent: Jun. 5, 2007

(54) METHOD OF PERFORMING A TRANSFORAMINAL POSTERIOR LUMBER INTERBODY FUSION PROCEDURE

(75) Inventors: David Gerber, CH-Arborn (CH); Dominique Messerli, West Chester, PA (US); David Paul, Phoenixville, PA (US)

(73) Assignee: Synthes (U.S.A.), West Chester, PA (US)

( * ) Notice: Subject to any disclaimer, the term of this patent is extended or adjusted under 35 U.S.C. 154(b) by 479 days.

(21) Appl. No.: 10/788,015

(22) Filed: Feb. 26, 2004

(65) Prior Publication Data

US 2004/0167538 A1    Aug. 26, 2004

Related U.S. Application Data

(62) Division of application No. 09/848,178, filed on May 3, 2001, now Pat. No. 6,719,794.

(51) Int. Cl.
*A61F 2/44* (2006.01)
*A61B 19/00* (2006.01)
*A61B 17/56* (2006.01)

(52) U.S. Cl. .................................. 623/17.16; 128/898

(58) Field of Classification Search ... 623/17.11–17.16
See application file for complete search history.

(56) References Cited

U.S. PATENT DOCUMENTS

| | | |
|---|---|---|
| 3,875,595 A | 4/1975 | Froning |
| 4,349,921 A | 9/1982 | Kuntz |
| 4,535,485 A | 8/1985 | Ashman et al. |
| 4,636,217 A | 1/1987 | Ogilvie et al. |
| 4,743,256 A | 5/1988 | Brantigan |
| 4,772,287 A | 9/1988 | Ray et al. |
| 4,790,297 A | 12/1988 | Luque |
| 4,820,305 A | 4/1989 | Harms et al. |
| 4,834,757 A | 5/1989 | Brantigan |
| 4,878,915 A | 11/1989 | Brantigan |

(Continued)

FOREIGN PATENT DOCUMENTS

EP            0 307 241           3/1989

(Continued)

OTHER PUBLICATIONS

Regeneration Technologies, Inc. Catalog, Nov. 1999.

(Continued)

*Primary Examiner*—Tom Barrett
(74) *Attorney, Agent, or Firm*—Stroock & Stroock & Lavan LLP

(57) ABSTRACT

An intervertebral implant for fusing vertebrae is disclosed. The implant has a body with curved, substantially parallel posterior and anterior faces separated by two narrow implant ends, superior and inferior faces having a plurality of undulating surfaces for contacting upper and lower vertebral endplates, and at least one depression at a first end for engagement by an insertion tool. The arcuate implant configuration facilitates insertion of the implant from a transforaminal approach into a symmetric position about the midline of the spine so that a single implant provides balanced support to the spinal column. The implant may be formed of a plurality of interconnecting bodies assembled to form a single unit. An implantation kit and method are also disclosed.

32 Claims, 14 Drawing Sheets

U.S. PATENT DOCUMENTS

| | | | |
|---|---|---|---|
| 4,917,704 A | 4/1990 | Frey et al. |
| 4,961,740 A | 10/1990 | Ray et al. |
| 4,969,888 A | 11/1990 | Scholten et al. |
| 5,026,373 A | 6/1991 | Ray et al. |
| 5,055,104 A | 10/1991 | Ray |
| 5,059,193 A | 10/1991 | Kuslich |
| 5,071,437 A | 12/1991 | Steffee |
| 5,123,926 A | 6/1992 | Pisharodi |
| 5,192,327 A | 3/1993 | Brantigan |
| 5,222,987 A | 6/1993 | Jones |
| 5,261,913 A | 11/1993 | Marnay |
| 5,282,862 A | 2/1994 | Baker et al. |
| 5,294,391 A | 3/1994 | McMillin |
| 5,306,309 A | 4/1994 | Wagner et al. |
| 5,336,699 A | 8/1994 | Cooke et al. |
| 5,395,317 A | 3/1995 | Kambin |
| 5,397,364 A | 3/1995 | Kozak et al. |
| 5,405,402 A | 4/1995 | Dye et al. |
| 5,407,445 A | 4/1995 | Tautvydas et al. |
| 5,423,825 A | 6/1995 | Levine |
| 5,425,772 A | 6/1995 | Brantigan |
| 5,429,863 A | 7/1995 | McMillin |
| 5,443,514 A | 8/1995 | Steffee |
| 5,458,638 A | 10/1995 | Kuslich et al. |
| 5,458,642 A | 10/1995 | Beer et al. |
| 5,474,555 A | 12/1995 | Puno et al. |
| 5,476,880 A | 12/1995 | Cooke et al. |
| 5,480,442 A | 1/1996 | Bertagnoli |
| 5,489,307 A | 2/1996 | Kuslich et al. |
| 5,489,308 A | 2/1996 | Kuslich et al. |
| 5,514,180 A | 5/1996 | Heggeness et al. |
| 5,522,899 A | 6/1996 | Michelson |
| 5,562,736 A | 10/1996 | Ray et al. |
| 5,571,103 A | 11/1996 | Bailey |
| 5,609,635 A | 3/1997 | Michelson |
| 5,609,636 A | 3/1997 | Kohrs et al. |
| 5,618,286 A | 4/1997 | Brinker |
| 5,645,596 A | 7/1997 | Kim et al. |
| 5,658,335 A | 8/1997 | Allen |
| 5,669,909 A | 9/1997 | Zdeblick et al. |
| 5,674,295 A | 10/1997 | Ray et al. |
| 5,676,146 A | 10/1997 | Scarborough |
| 5,683,463 A | 11/1997 | Godefroy et al. |
| 5,683,464 A | 11/1997 | Wagner et al. |
| 5,709,685 A | 1/1998 | Dombrowski et al. |
| 5,716,415 A | 2/1998 | Steffee |
| 5,741,261 A | 4/1998 | Moskovitz et al. |
| 5,755,797 A | 5/1998 | Baumgartner |
| 5,766,252 A | 6/1998 | Henry et al. |
| 5,782,919 A | 7/1998 | Zdeblick et al. |
| 5,820,918 A | 10/1998 | Ronan et al. |
| 5,824,077 A | 10/1998 | Mayer |
| 5,824,094 A | 10/1998 | Serhan et al. |
| 5,860,973 A | 1/1999 | Michelson |
| 5,865,845 A | 2/1999 | Thalgott |
| 5,865,846 A | 2/1999 | Bryan et al. |
| 5,868,745 A | 2/1999 | Alleyne |
| 5,876,457 A | 3/1999 | Picha et al. |
| 5,885,300 A | 3/1999 | Tokuhashi et al. |
| 5,888,224 A | 3/1999 | Beckers et al. |
| 5,888,227 A | 3/1999 | Cottle |
| 5,897,593 A | 4/1999 | Kohrs et al. |
| 5,904,719 A | 5/1999 | Errico et al. |
| 5,913,896 A | 6/1999 | Boyle et al. |
| 5,919,235 A | 7/1999 | Husson et al. |
| 5,954,724 A | 9/1999 | Davidson |
| 5,961,554 A | 10/1999 | Janson et al. |
| 5,984,922 A | 11/1999 | McKay |
| 5,989,289 A | 11/1999 | Coates et al. |
| 6,019,793 A | 2/2000 | Perren et al. |
| 6,025,538 A | 2/2000 | Yaccarino, III |
| 6,033,438 A | 3/2000 | Bianchi et al. |
| 6,039,762 A | 3/2000 | McKay |
| 6,042,582 A | 3/2000 | Ray |
| 6,059,790 A | 5/2000 | Sand et al. |
| 6,059,829 A | 5/2000 | Schläpfer et al. |
| 6,074,423 A | 6/2000 | Lawson |
| 6,080,158 A | 6/2000 | Lin |
| 6,086,613 A | 7/2000 | Camino et al. |
| 6,113,602 A | 9/2000 | Sand |
| 6,113,638 A | 9/2000 | Williams et al. |
| 6,136,031 A | 10/2000 | Middleton |
| 6,143,032 A | 11/2000 | Schafer et al. |
| 6,143,033 A | 11/2000 | Paul et al. |
| 6,156,040 A | 12/2000 | Yonemura et al. |
| 6,159,211 A | 12/2000 | Boriani et al. |
| 6,159,212 A | 12/2000 | Schoedinger et al. |
| 6,174,311 B1 | 1/2001 | Branch et al. |
| 6,200,347 B1 | 3/2001 | Anderson et al. |
| 6,241,769 B1 | 6/2001 | Nicholson et al. |
| 6,245,108 B1 | 6/2001 | Biscup |
| 6,261,586 B1 | 7/2001 | McKay |
| 6,296,664 B1 | 10/2001 | Middleton |
| 6,315,797 B1 | 11/2001 | Middleton |
| 6,342,074 B1 | 1/2002 | Simpson |
| 6,350,283 B1 | 2/2002 | Michelson |
| 6,371,988 B1 | 4/2002 | Pafford et al. |
| 6,387,130 B1 * | 5/2002 | Stone et al. ............. 623/17.16 |
| 6,395,035 B2 | 5/2002 | Bresina et al. |
| 6,423,095 B1 | 7/2002 | Van Hoeck et al. |
| 6,432,106 B1 | 8/2002 | Fraser |
| 6,447,544 B1 | 9/2002 | Michelson |
| 6,454,805 B1 | 9/2002 | Baccelli et al. |
| 6,458,159 B1 | 10/2002 | Thalgott |
| 6,575,899 B1 * | 6/2003 | Foley et al. ................ 600/114 |
| 6,830,570 B1 * | 12/2004 | Frey et al. .................... 606/61 |
| 2001/0008980 A1 | 7/2001 | Gresser et al. |
| 2001/0012966 A1 | 8/2001 | Studer et al. |
| 2001/0016774 A1 | 8/2001 | Bresina et al. |
| 2001/0016777 A1 | 8/2001 | Biscup |
| 2001/0031967 A1 | 10/2001 | Nicholson et al. |
| 2002/0004683 A1 | 1/2002 | Michelson |
| 2002/0013624 A1 | 1/2002 | Michelson |
| 2002/0019637 A1 | 2/2002 | Frey et al. |
| 2002/0022886 A1 | 2/2002 | Fuss et al. |
| 2002/0026243 A1 | 2/2002 | Lin |
| 2002/0055781 A1 | 5/2002 | Sazy |
| 2002/0065558 A1 | 5/2002 | Varga et al. |
| 2002/0065560 A1 | 5/2002 | Varga et al. |
| 2002/0077700 A1 | 6/2002 | Varga et al. |
| 2002/0082597 A1 | 6/2002 | Fraser |
| 2002/0087212 A1 | 7/2002 | James et al. |
| 2002/0091447 A1 | 7/2002 | Shimp et al. |
| 2002/0099376 A1 | 7/2002 | Michelson |
| 2002/0099444 A1 | 7/2002 | Boyd et al. |
| 2002/0107573 A1 | 8/2002 | Steinberg |

FOREIGN PATENT DOCUMENTS

| | | |
|---|---|---|
| EP | 0 551 574 | 7/1993 |
| EP | 0 599 419 A2 | 12/1993 |
| EP | 0 834 295 | 4/1998 |
| EP | 0 916 323 A1 | 5/1999 |
| FR | 2 736 537 | 12/1995 |
| FR | 2 724 312 | 3/1996 |
| FR | 2 727 003 | 5/1996 |
| FR | 2 727 004 | 5/1996 |
| FR | 2 727 005 | 5/1996 |
| FR | 2 736 538 | 1/1997 |
| JP | 8010275 | 1/1996 |
| JP | 8010276 | 1/1996 |
| JP | 2001170092 | 6/2001 |
| WO | WO 89/09035 | 10/1989 |
| WO | WO 96/25086 | 8/1996 |

| | | |
|---|---|---|
| WO | WO 96/40014 | 12/1996 |
| WO | WO 97/15248 | 5/1997 |
| WO | WO 99/09914 | 3/1999 |
| WO | WO 99/37255 | 7/1999 |
| WO | WO 00/07527 | 2/2000 |
| WO | WO 00/74608 | 12/2000 |
| WO | WO 01/28469 A2 | 4/2001 |
| WO | WO 01/28469 A3 | 4/2001 |
| WO | WO 01/70144 A1 | 9/2001 |
| WO | WO 01/95838 A1 | 12/2001 |

OTHER PUBLICATIONS

Sofamor Danek Surgical Technique for Tangent Posterior Discectomy & Grafting Instrumentation, Set, 1999.
PCT International Search Report PCT/US 02/14086.
Depuy Acromed Devex System Product Ordering Guide, Jan. 2003.

* cited by examiner

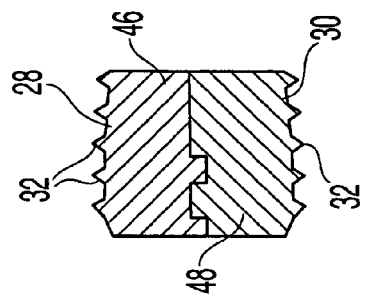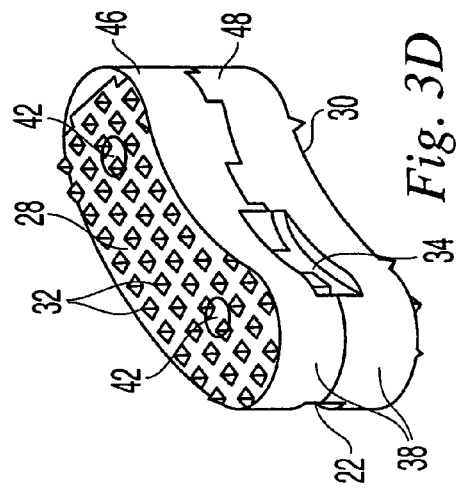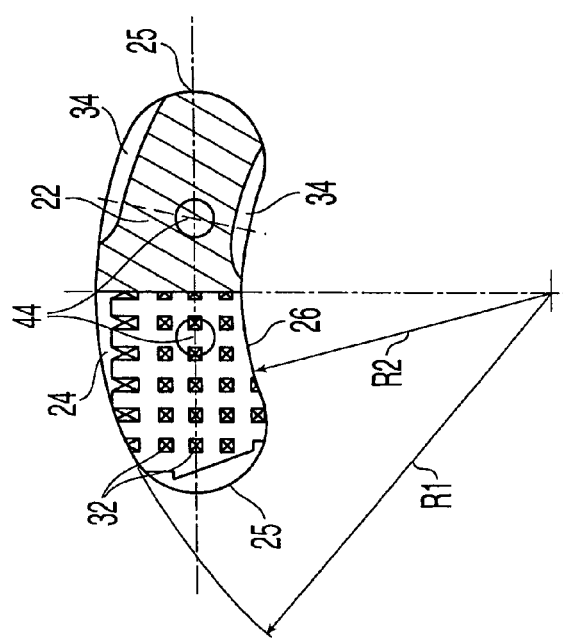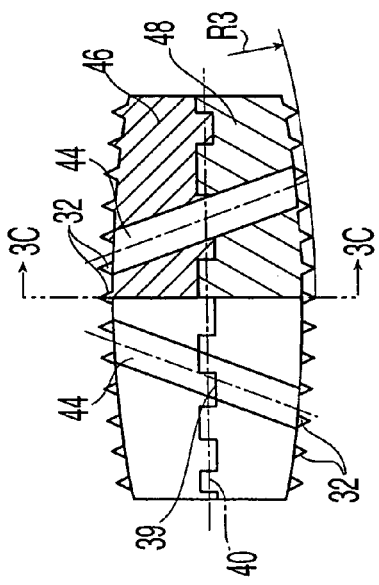

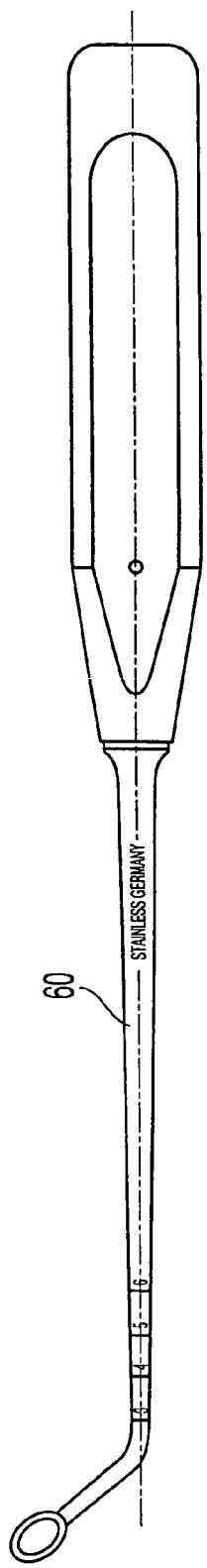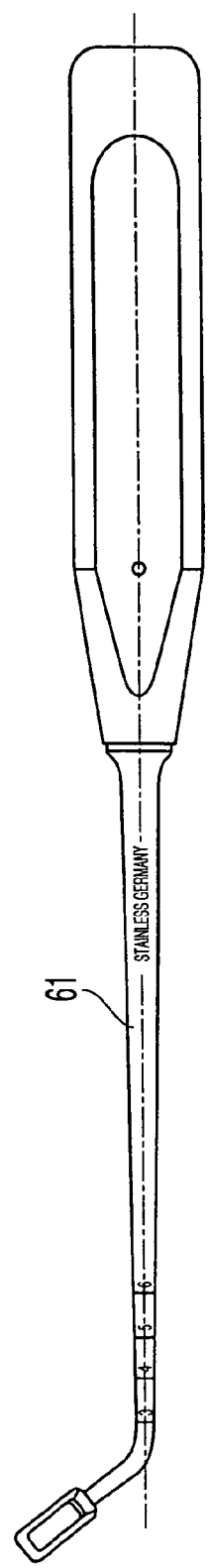
Fig. 8A
Fig. 8B

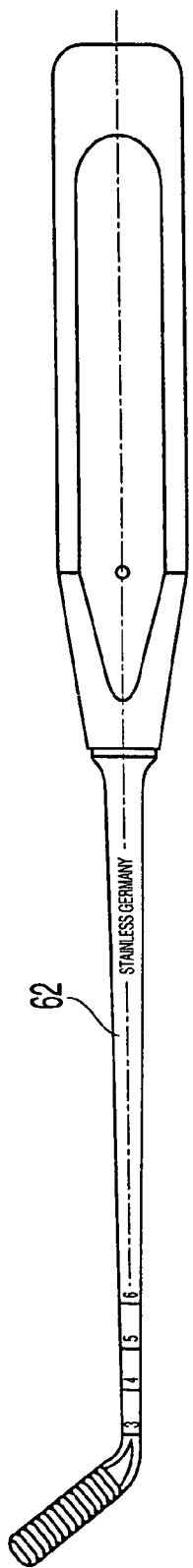
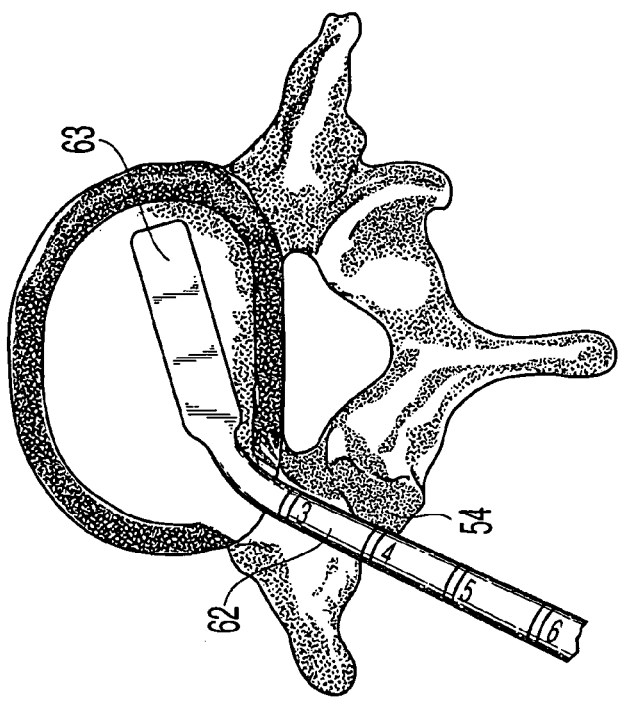
Fig. 9A
Fig. 9B

METHOD OF PERFORMING A TRANSFORAMINAL POSTERIOR LUMBER INTERBODY FUSION PROCEDURE

CROSS-REFERENCE TO RELATED APPLICATIONS

The present application is a divisional of U.S. patent application Ser. No. 09/848,178, filed May 3, 2001, now U.S. Pat. No. 6,719,794, the contents of which is expressly incorporated herein by reference thereto.

FIELD OF THE INVENTION

The present invention is directed to an intervertebral implant, its accompanying instrumentation and their method of use. More particularly, the present invention is directed to an intervertebral implant and instrumentation for use in a transforaminal posterior lumbar interbody fusion procedure.

BACKGROUND OF THE INVENTION

A number of medical conditions such as compression of spinal cord nerve roots, degenerative disc disease, herniated nucleus pulposis, spinal stenosis and spondylolisthesis can cause severe low back pain. Intervertebral fusion is a surgical method of alleviating low back pain. In posterior lumbar interbody fusion ("PLIF"), two adjacent vertebral bodies are fused together by removing the affected disc and inserting one or more implants that would allow for bone to grow between the two vertebral bodies to bridge the gap left by the disc removal.

One variation of the traditional PLIF technique is the transforaminal posterior lumbar interbody fusion (T-PLIF) technique. Pursuant to this procedure, an implant is inserted into the affected disc space via a unilateral (or sometimes bilateral), posterior approach, offset from the midline of the spine, by removing the facet joint of the vertebrae. The T-PLIF approach avoids damage to nerve structures such as the dura and the nerve root, but the resulting transforaminal window available to remove the affected disc, prepare the vertebral endplates, and insert the implant is limited laterally.

A number of different implants typically used for the traditional PLIF procedure have been used for the T-PLIF procedure, with varying success. These include threaded titanium cages, allograft wedges, rings, etc. However, as these devices were not designed specifically for the T-PLIF procedure, they are not shaped to be easily insertable into the affected disc space through the narrow transforaminal window, and may require additional retraction of nerve roots. Such retraction can cause temporary or permanent nerve damage. In addition, some of these implants, such as the threaded titanium cage, suffer from the disadvantage of requiring drilling and tapping of the vertebral endplates for insertion. Further, the incidence of subsidence in long term use is not known for such cages. Finally, restoration of lordosis, i.e., the natural curvature of the lumbar spine is very difficult when a cylindrical titanium cage is used.

As the discussion above illustrates, there is a need for an improved implant and instrumentation for fusing vertebrae via the transforaminal lumbar interbody fusion procedure.

SUMMARY OF THE INVENTION

The present invention relates to an intervertebral implant ("T-PLIF implant") and its use during a transforaminal lumbar interbody fusion procedure. In a preferred embodiment, the T-PLIF implant has an arcuate body with curved, substantially parallel posterior and anterior faces separated by two narrow implant ends, and superior and inferior faces having a plurality of undulating surfaces for contacting upper and lower vertebral endplates. The undulating surfaces may be projections, such as teeth, of a saw-tooth or pyramidal configuration, or ridges which penetrate the vertebral endplates and prevent slippage. The narrow implant ends may be rounded or substantially flat. The arcuate implant configuration facilitates insertion of the implant via a transforaminal window. The implant, which may be formed of allogenic bone, metal, or plastic, may also have at least one depression, such as a channel or groove, at a first end for engagement by an insertion tool, such as an implant holder. In a preferred aspect, the superior and inferior faces are convex, and the thickness of the implant tapers with its greatest thickness in the middle region between the narrow ends of the implant, i.e., at a section parallel to a sagittal plane, and decreasing toward each of the narrow ends.

In another preferred embodiment, the implant is formed of a plurality of interconnecting bodies assembled to form a single unit. In this configuration, the plurality of interconnecting bodies forming the T-PLIF implant may be press-fit together and may include at least one pin or screw extending through an opening in the plurality of bodies to hold the bodies together as a single unit. Adjacent surfaces of the plurality of bodies may also have mating interlocking surfaces that aid in holding the bodies together as a single unit.

In still another preferred embodiment, the present invention relates to a kit for implanting an intervertebral implant into an affected disc space of a patient via a transforaminal window. The kit includes an implant having an arcuate body with curved, substantially parallel posterior and anterior faces separated by two narrow implant ends, superior and inferior faces preferably having a plurality of undulating surfaces, such as projections or teeth, for contacting upper and lower vertebral endplates. The superior and inferior faces may define a thickness. Preferably the implant has at least one depression at a first end for engagement by an insertion tool. The kit may further include at least one trial-fit spacer for determining the appropriate size of the implant needed to fill the affected disc space, an insertion tool having an angled or curved neck for holding and properly positioning the implant during insertion through the transforaminal window, and an impactor having an angled or curved neck for properly positioning the implant within the affected disc space. The face of the impactor may be concavely shaped to mate with the narrow end of the T-PLIF implant during impaction. The kit may further include a lamina spreader for distracting vertebrae adjacent to the affected disc space, an osteotome for removing facets of the vertebrae adjacent to the affected disc space to create a transforaminal window, one or more curettes, angled and/or straight, for removing all disc material from the affected disc space, a bone rasp for preparing endplates of the vertebrae adjacent the affected disc space, and a graft implant tool for implanting bone graft material into the affected disc space. The kit may still further include a curved guide tool to guide the implant into the affected disc space.

In yet another aspect, a method for implanting an intervertebral implant into an affected disc space of a patient via a transforaminal window is described. The transforaminal window is created and bone graft material is inserted into the affected disc space. Using an insertion tool, an implant is inserted into the affected disc space via the transforaminal window, the implant having an arcuate body with curved, substantially parallel posterior and anterior faces separated by two narrow implant ends, superior and inferior faces having a plurality of undulating surfaces for contacting upper and lower vertebral endplates, and preferably at least one depression at a first end for engagement by the insertion tool. In the present method, the arcuate implant configuration facilitates insertion of the implant via the transforaminal window. The method may further comprise impacting the implant with an impactor tool to properly position the implant within the affected disc space. Either or both the insertion tool and the impactor tool may be angled to facilitate insertion, alignment, placement and/or proper seating of the implant.

BRIEF DESCRIPTION OF THE DRAWINGS

FIG. 3A is a partial cross-section view of another embodiment of an implant according to the present invention;

FIG. 3B is a partial cross-section view along the longer axis of the implant of FIG. 3A;

FIG. 3C is a cross-section view taken along line 3C—3C of FIG. 3B;

FIG. 3D is a perspective view of the implant of FIG. 3A;

FIG. 8A depicts an angled bone curette for use during the T-PLIF procedure;

FIG. 8B depicts another angled bone curette for use during the T-PLIF procedure;

FIG. 9A depicts an angled bone rasp for use during a T-PLIF procedure;

FIG. 9B depicts an angled bone rasp removing material from an affected disc space;

DESCRIPTION OF THE PREFERRED EMBODIMENTS

Figure 1:
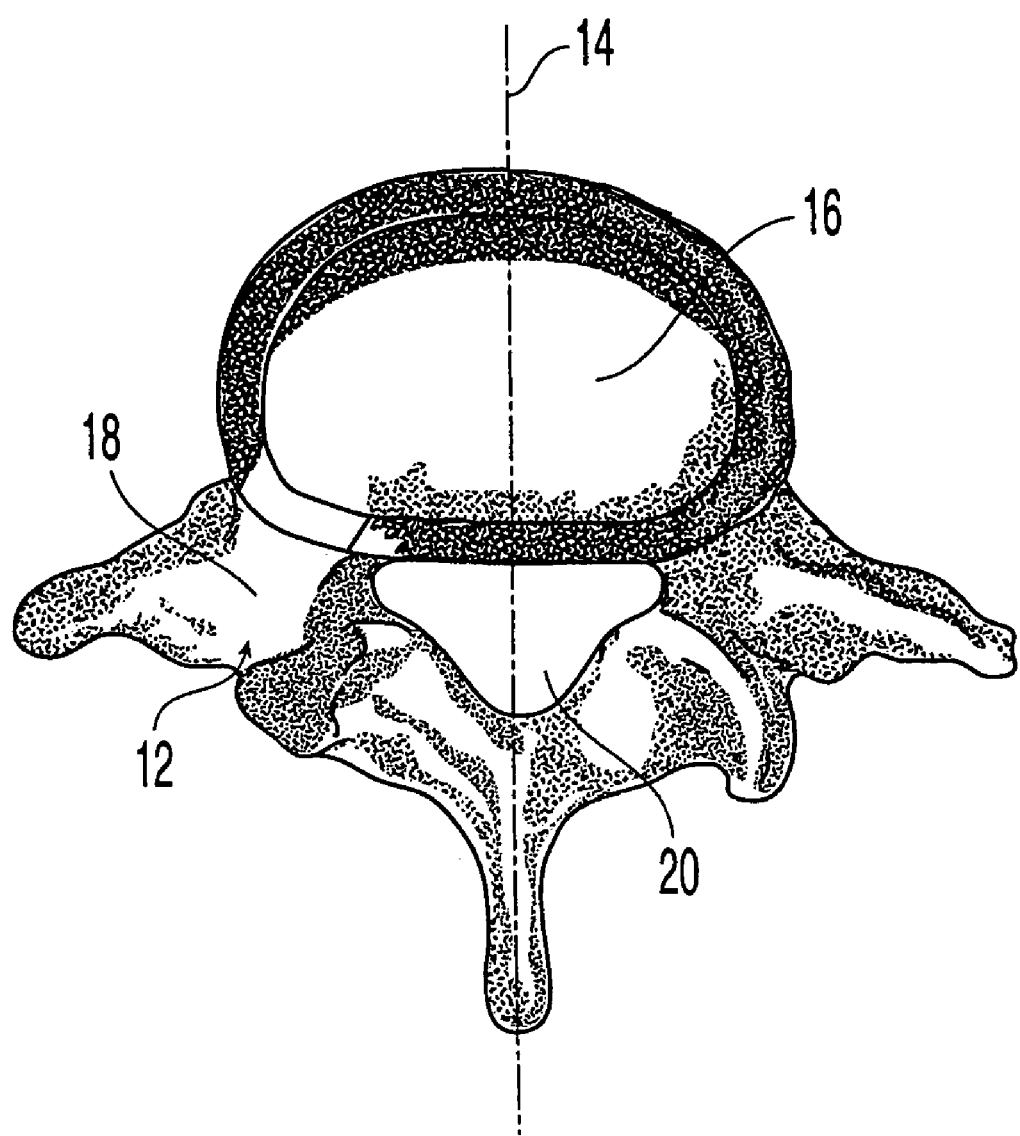
FIG. 1 is a top view of a typical human vertebrae showing the transforaminal window through which an implant according to the present invention is inserted.

An implant according to the present invention, referred to herein as a transforaminal posterior lumbar interbody fusion implant ("T-PLIF implant"), is designed for use as an intervertebral spacer in spinal fusion surgery, where an affected disk is removed from between two adjacent vertebrae and replaced with an implant that provides segmental stability and allows for bone to grow between the two vertebrae to bridge the gap created by disk removal. Specifically, the T-PLIF implant is designed for the transforaminal lumbar interbody fusion (T-PLIF) technique, which, as shown in FIG. 1, involves a posterior approach 12, offset from the midline 14 of the spine, to the affected intervertebral disk space 16. The window 18 available for implant insertion using the T-PLIF technique is limited laterally by the dura 20 and the superior exiting nerve root (not shown).

Figure 11A:
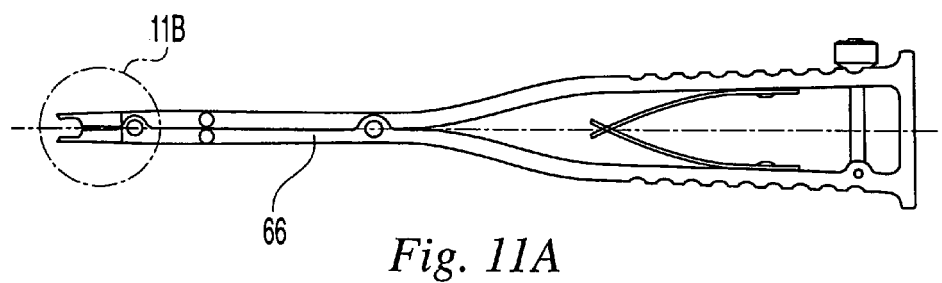
FIG. 11A depicts an implant holder for use during a T-PLIF procedure.
Figure 11B:
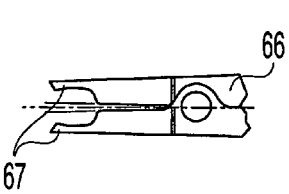
FIG. 11B depicts the tips of the implant holder shown in FIG. 11A.

As shown in FIGS. 2A through 2D, in a preferred embodiment, the T-PLIF implant has an arcuate, "rocker-like" body 22 with curved anterior and posterior faces 24, 26 to facilitate the offset insertion of the implant through the narrow approach window 18 into the disk space. Preferably, the anterior and posterior faces 24 and 26 are substantially parallel, separated by a pair of narrow ends 25. Narrow ends 25 may be rounded or blunt. The superior and inferior surfaces 28, 30 have projections, such as teeth 32, for engaging the adjacent vertebrae. Teeth 32 on superior and inferior surfaces 28, 30 preferably provide a mechanical interlock between implant 22 and the end plates by penetrating the end plates. The initial mechanical stability afforded by teeth 32 minimizes the risk of post-operative expulsion/slippage of implant 10. Teeth 32 may have a saw-tooth shape, where one side of the tooth is perpendicular to the superior or inferior surface, or a pyramid shape, where each tooth has four sides and forms an acute angle with the superior or inferior face. Preferably, implant body 22 has at least one channel or slot 34 on one end of implant 22 for engagement by a surgical instrument, such as an implant holder 66 (shown in FIG. 11A). It should be noted that implant 22 may also be configured with a channel 34 on only one side or without channels altogether. Other known methods for engaging the surgical instruments with the implant, such as a threaded bore for receiving the threaded end of a surgical tool, may also be used.

Figure 2A:
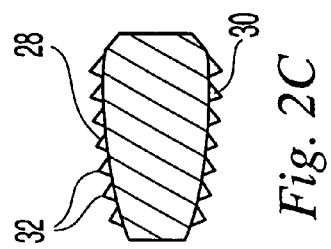
FIG. 2A is a cross-section view of an embodiment of an implant according to the present invention.
Figure 2B:
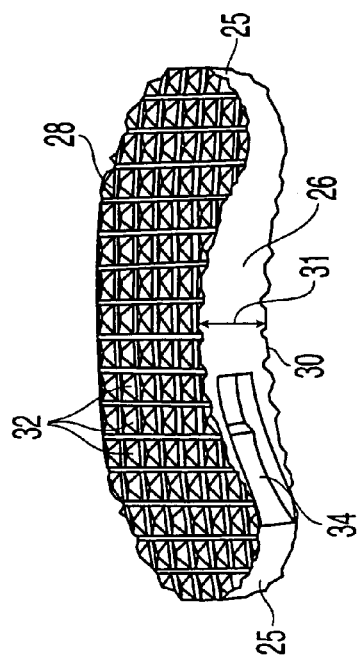
FIG. 2B is a side view along the longer axis of the implant of FIG. 2A.
Figure 2C:
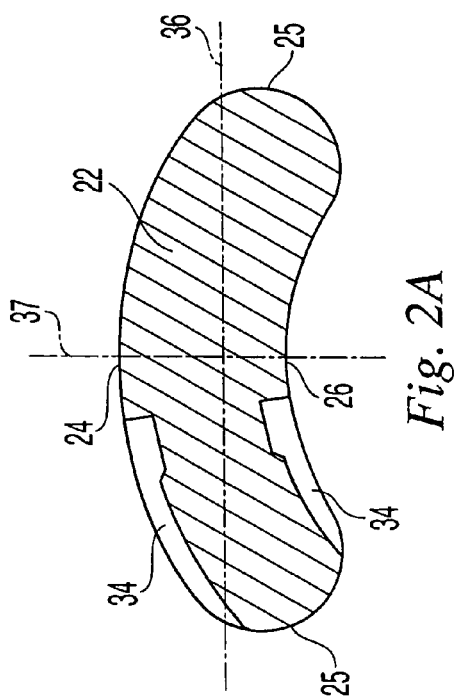
FIG. 2C is a cross-section view taken along line 2C—2C of FIG. 2B.
Figure 2D:
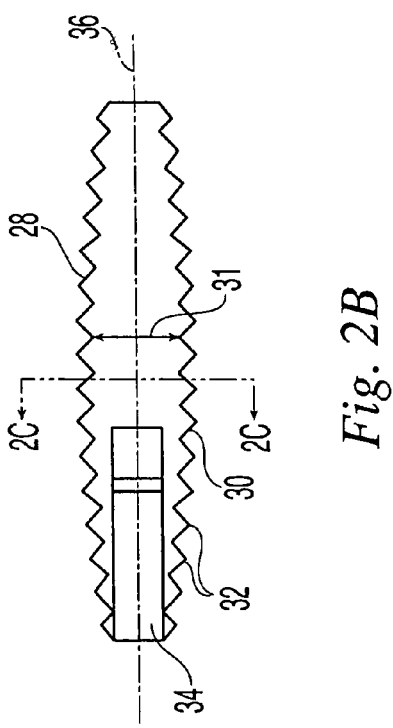
FIG. 2D is a perspective view of the implant of FIG. 2A.

As shown in FIG. 2B, thickness 31 of implant 22 is greatest at the mid-section between the two narrow implant ends 25 and tapers gradually along the longitudinal axis 36 of implant 22 so that it is thinnest at the narrow ends 25 of implant 22. This convex configuration provides a proper anatomical fit and facilitates insertion of implant 22 into the affected disc space. It should be noted that in a preferred embodiment, thickness 31 does not taper along the shorter axis 37 of implant 22. Thus, as shown in FIG. 2C for any given cross section taken perpendicular to the longitudinal axis 36 of the implant, the distance between the superior and inferior surfaces 28 and 30 remains substantially constant. In alternate embodiments, however, thickness 31 may taper along shorter axis 37 of implant 22. The dimensions of implant 22 can be varied to accommodate a patient's anatomy, and the thickness of the implant is chosen based on the size of the disk space to be filled. Preferably, implant 22 has a maximum thickness 31 at its mid-section of about 7.0 to about 17.0 mm, and may be formed of metal, allograft, a metal-allograft composite, a carbon-fiber polymer, pure polymer or plastic. The thickness at the narrow ends 25 of implant 22 may range from about 1.5 to about 2.0 mm less than the maximum thickness at the mid-section. The implant may range from about 26 to about 32 mm in length, and have a width from about 9 to 11 mm. Implant 22, which as shown most clearly in FIG. 2A is symmetric about at least one axis of rotation 37, is intended for symmetric placement about the midline 14 of the spine (see FIG. 19). The arcuate configuration of implant 22 facilitates insertion of the implant from the transforaminal approach into a symmetric position about the midline of the spine so that a single implant provides balanced support to the spinal column.

As shown in FIGS. 3A–3D, in an alternate embodiment implant 22 may be formed of two or more pieces 38 having interlocking grooves 39 and pallets 40 that are press-fit and fastened together with pins or screws 42. The number and orientation of pins or screws 42 can be varied. This multi-component configuration may be particularly useful for implants formed of allograft bone, since it may be difficult and/or impractical to obtain a single, sufficiently large piece of allograft for some applications. In the case of implants formed completely of artificial (i.e., non-allograft) materials, such as steel, plastic or metallic or non-metallic polymer, a one-piece implant may be more practical.

As in the previous embodiment, the anterior and posterior faces 24, 26 are substantially parallel, and, as shown, may be defined by radii of curvature R1 and R2, where R1, for example, may be in the range of about 28 mm and R2, for example, may be in the range of about 19 mm. The superior and inferior surfaces 28, 30 are arcuate shaped and the implant has a thickness 31, which is preferably greatest at a center portion between narrow ends 25 and gradually tapers becoming thinnest at narrow ends 25. Tapering thickness 31 may be defined by a radius of curvature R3, where R3 for example, may be in the range of about 100 mm. As shown, the component pieces 46, 48 of implant 22 have holes 44 to accommodate pins or screws 42. Holes 44 are preferably drilled after component pieces 38 have been stacked one on top of the other. The multiple pieces 38 are then assembled with screws or pins 42 so that practitioners receive the implant 22 as a single, pre-fabricated unit. The upper component piece 46 has an arcuate superior surface preferably with teeth 32, while its bottom surface is configured with grooves and pallets to interlock with the upper surface of lower component piece 48. The arcuate inferior surface 30 of lower component piece 48 also preferably has teeth 32 for engaging the lower vertebral endplate of the affected disc space. Either or both superior and inferior surfaces 28, 30 may have ridges or some other similar form of engaging projection in place of teeth 32.

Figure 4:
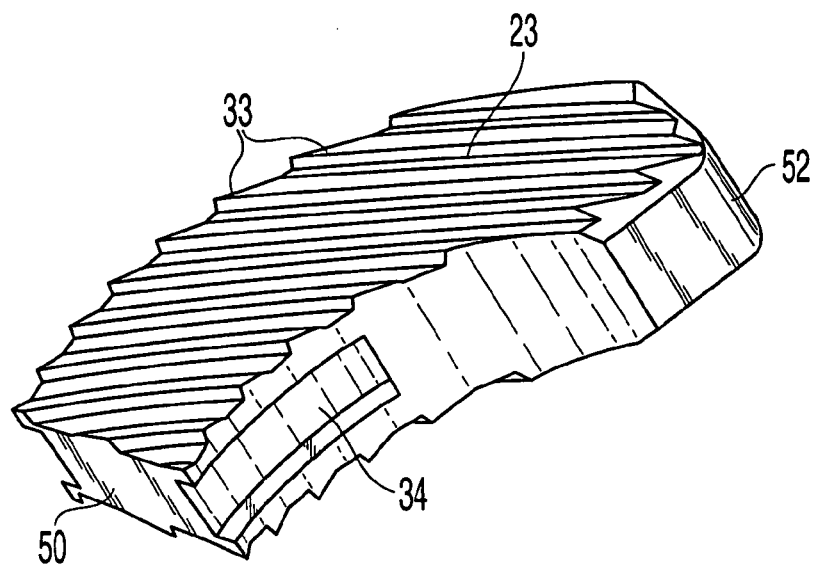
FIG. 4 is a perspective view of still another embodiment of the implant of the present invention.
Figure 5:
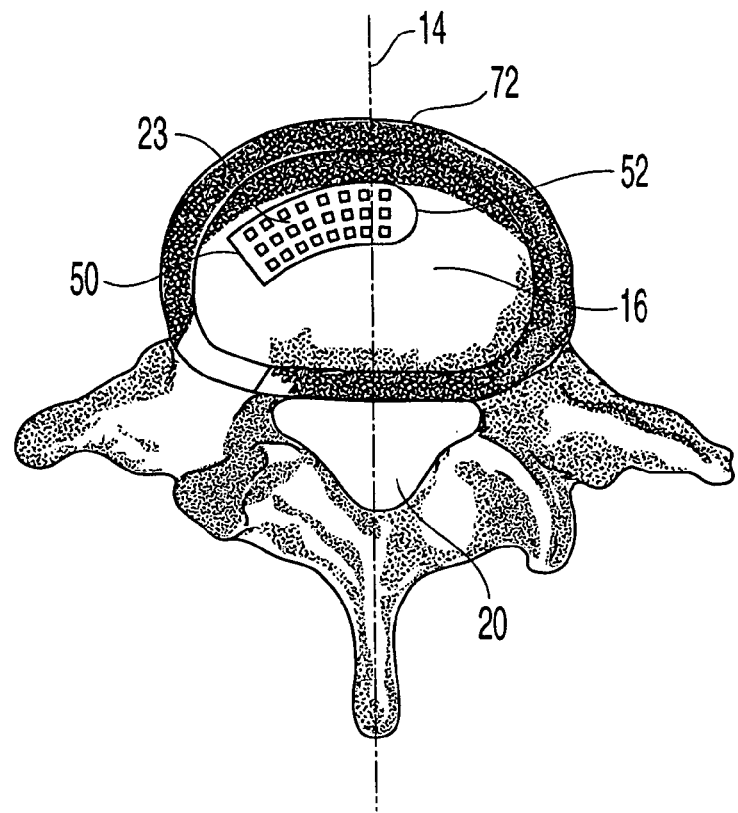
FIG. 5 is an axial view of a typical human vertebrae showing the implant of FIG. 4 in an asymmetric final position.

Reference is now made to FIG. 4 which is a perspective view of another embodiment an implant. As in the previous embodiment, implant 23 has a curved body with substantially parallel arcuate anterior and posterior faces 24, 26, convex superior and inferior surfaces 28, 30 contributing to a tapering thickness 31, and channels 34 for engaging a surgical instrument, such as an insertion tool. In this embodiment, implant 23 has a substantially straight or blunted narrow end 50 and a curved narrow end 52 separating parallel, arcuate anterior and posterior faces 24, 26. As shown in FIG. 5, the final position of implant 23 in disc space 16 may be asymmetric with respect to midline 14 of the patient's spine.

Figure 6:
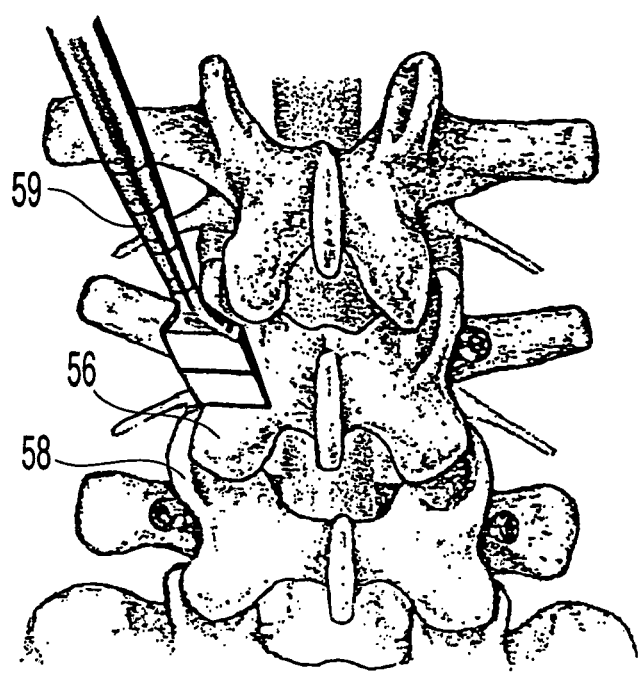
FIG. 6 is a posterior view of a section of human spine prior to preparation of the transforaminal window.
Figure 7:
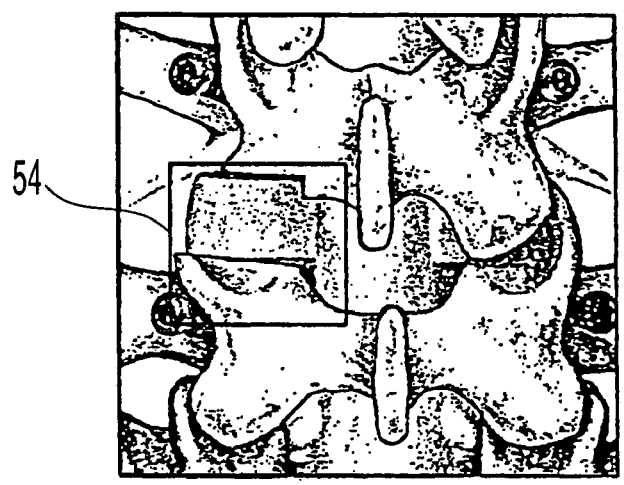
FIG. 7 is a posterior view of a section of human spine with the transforaminal window prepared.
Figure 8C:
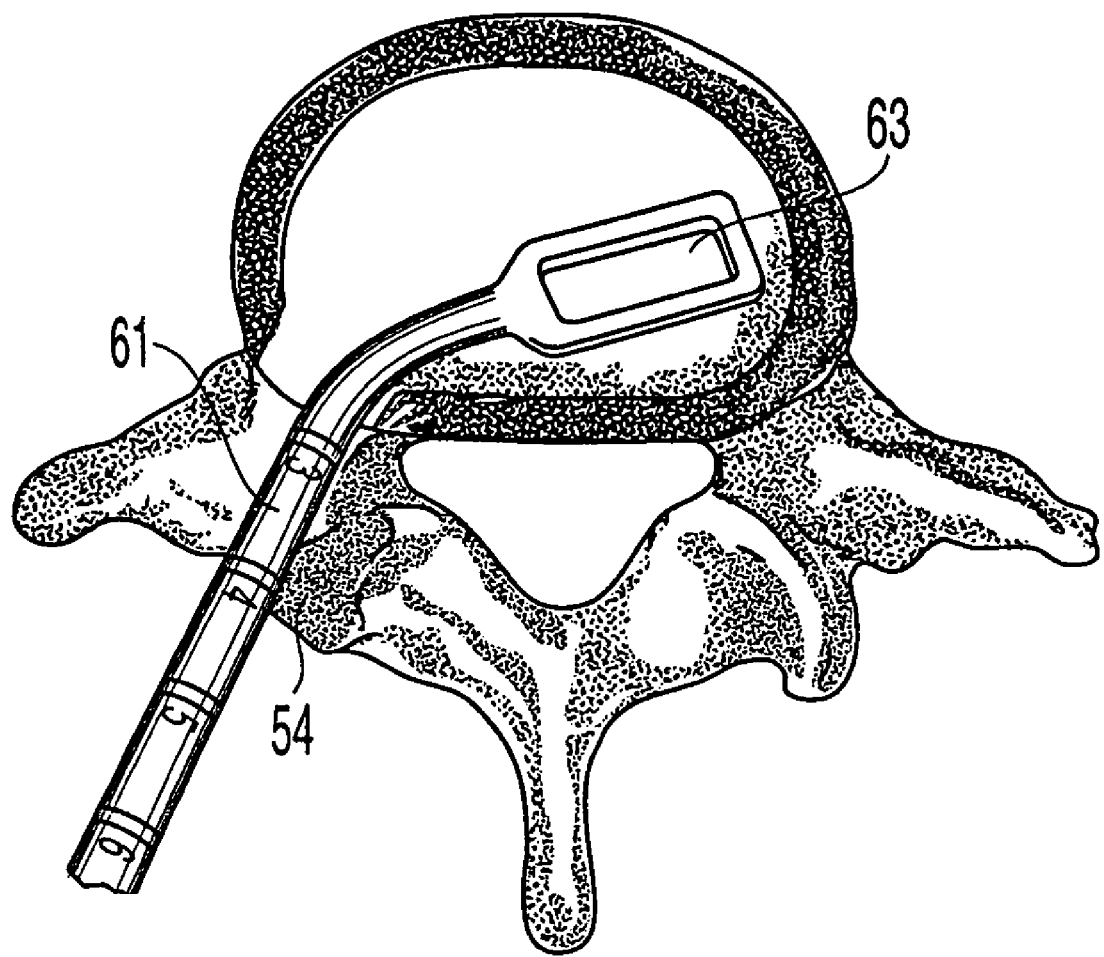
FIG. 8C depicts an angled bone curette removing disc material from an affected disc space.
Figure 11C:
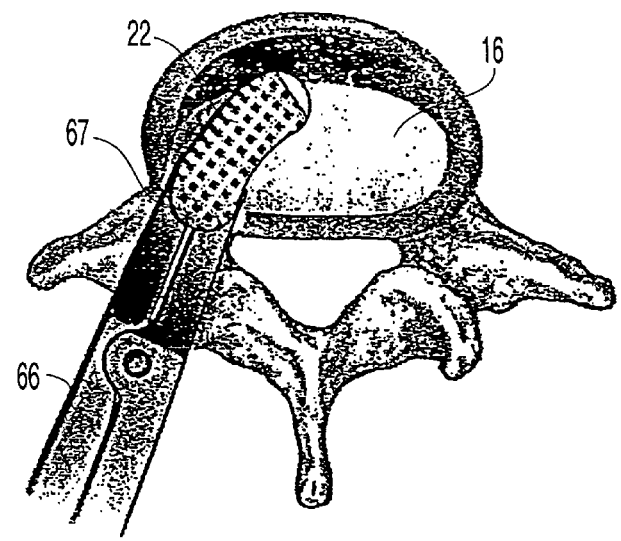
FIG. 11C depicts a top view of a human vertebrae showing a T-PLIF implant being inserted with in an implant holder.

As shown in FIGS. 2A & 3A, and FIG. 11C, the rocker-like shape of implant 22 enables the surgeon to insert the implant through the narrow transforaminal window, typically on the range of about 9.0 mm wide, and seat the implant in the disc space behind the dura without disturbing the anterior curtain of the disc space. The typical surgical technique for the T-PLIF procedure begins with the patient being placed in a prone position on a lumbar frame. Prior to incision, radiographic equipment can assist in locating the precise intraoperative position of the T-PLIF implant. Following incision, the facets, lamina and other anatomical landmarks are identified. The affected vertebrae are distracted using a lamina spreader or a lateral distractor, both of which are commonly known in the art. In the latter case, screws may be inserted into the vertebrae to interface with the lateral distractor. As shown in FIGS. 6 & 7, following distraction, the transforaminal window 54 is created by removing the inferior facet 56 of the cranial vertebrae and the superior facet 58 of the caudal vertebrae using one or more osteotomes 59 of different sizes. A discectomy is performed during which all disc material from the affected disc space may be removed using a combination of straight and angled curettes. Angled curettes, which may be configured with rounded profile 60 (FIG. 8A) or a rectangular profile 61 (FIG. 8B), enable removal of material on the far side 63 of the disc space opposite transforaminal window 54, as shown in FIGS. 8C.

Figure 10A:
FIG. 10A depicts a trial-fit spacer for use during a T-PLIF procedure.
Figure 10B:
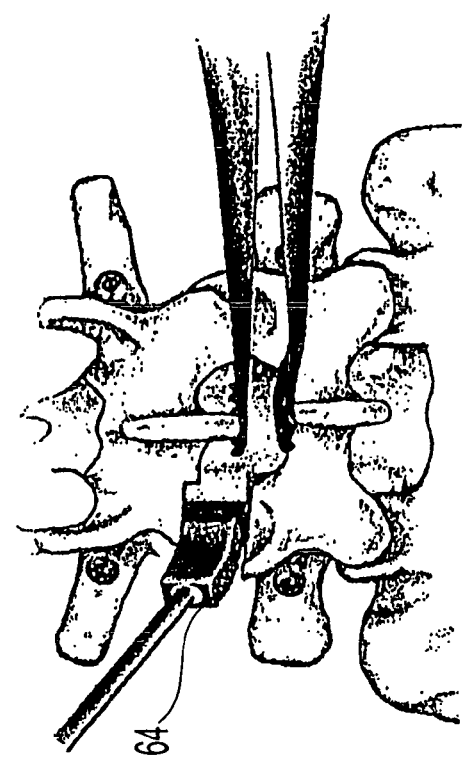
FIG. 10B depicts a trial-fit spacer being inserted into an affected disc space via a transforaminal window.

After the discectomy is complete, the superficial layers of the entire cartilaginous endplates are removed with a combination of straight and angled bone rasps. As shown in FIGS. 9A and 9B, angled rasps 62 may be angled to reach far side 63 of the disc space opposite transforaminal window 54. Rasps 62 expose bleeding bone, but care should be taken to avoid excess removal of subchondral bone, as this may weaken the anterior column. Entire removal of the endplate may result in subsidence and loss of segmental stability. Next, an appropriately sized trial-fit T-PLIF spacer/template 64, shown in FIGS. 10A and 10B, may be inserted into the intervertebral disc space using gentle impaction, to determine the appropriate implant thickness for the disc space to be filled. Fluoroscopy can assist in confirming the fit of the trial spacer. If the trial spacer 64 appears too loose/too tight, the next larger/smaller size trial spacer should be used until the most secure fit is achieved. For example, if a trial fit spacer with a maximum thickness of 11 mm is too loose when inserted into the disc space, a physician should try the 13 mm thick spacer, and so on. Trial fit spacers preferably range in height from about 7 mm to about 17 mm.

Figure 11D:
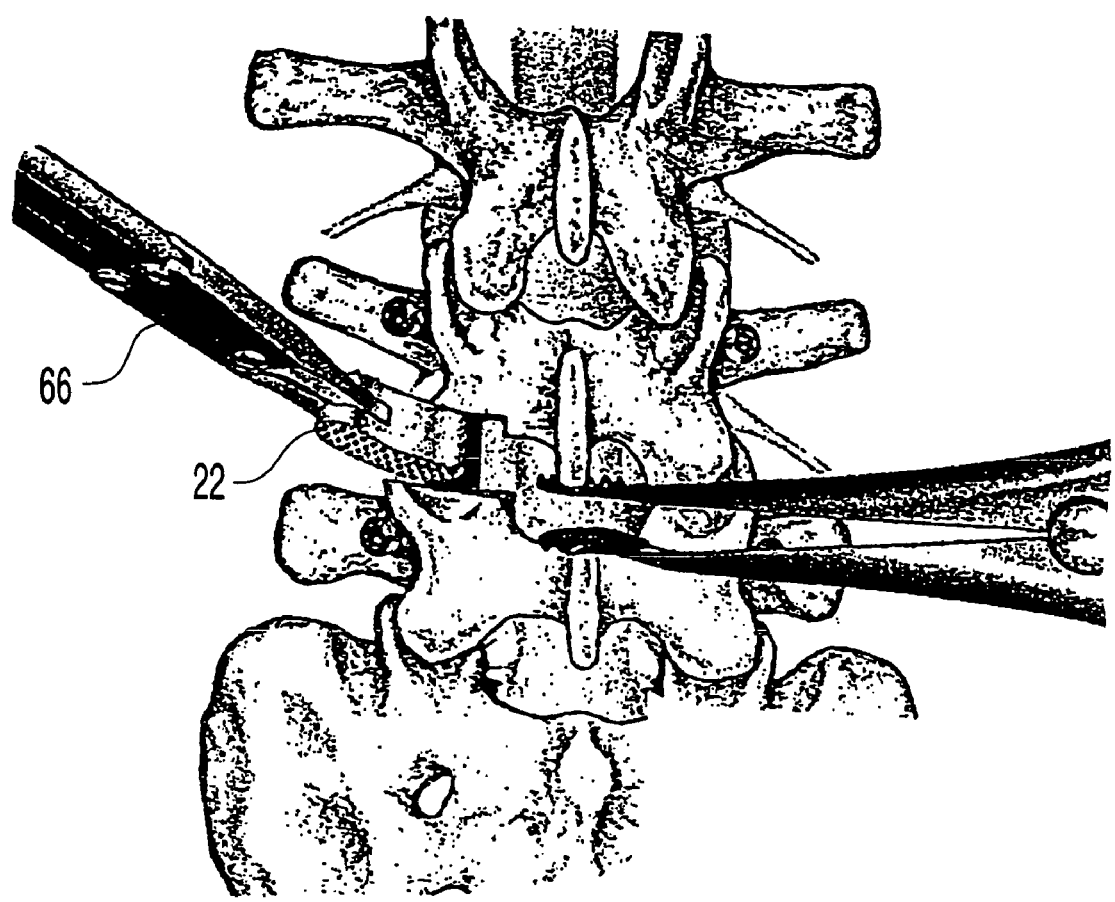
FIG. 11D depicts an posterior view of the human spine showing a T-PLIF implant being inserted with an implant holder.
Figure 12:
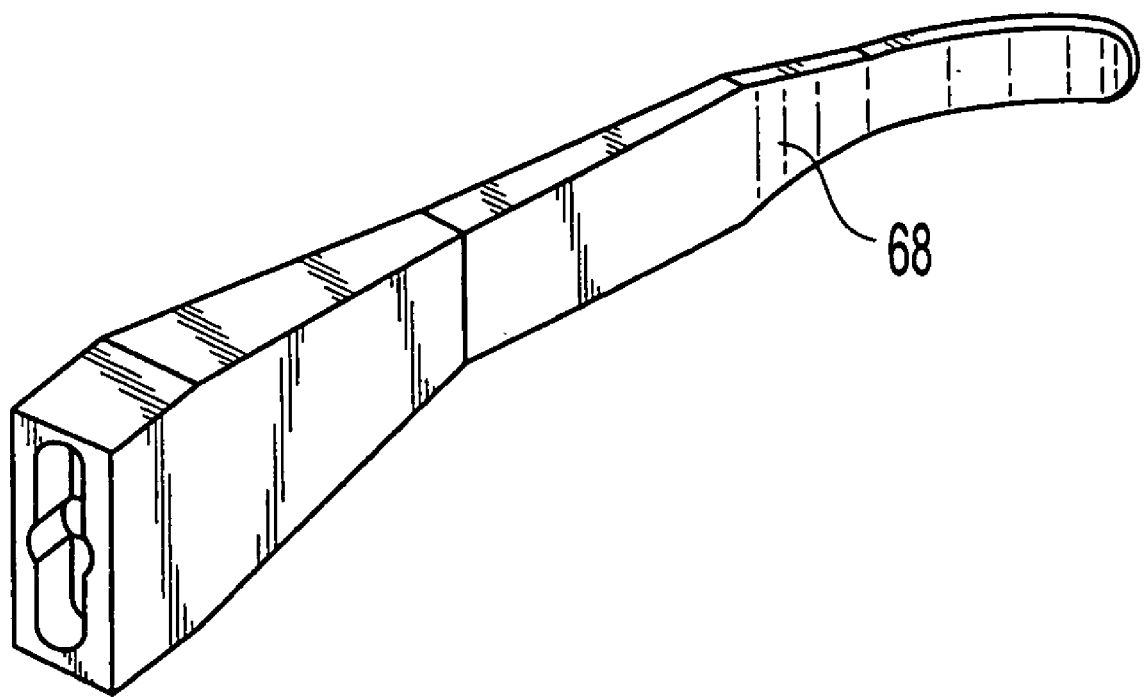
FIG. 12 depicts an implant guide tool for use with the T-PLIF implant.
Figure 13A:
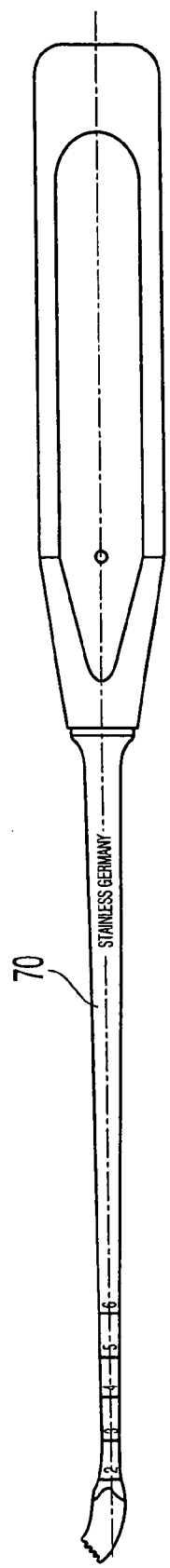
FIG. 13A depicts an angled impactor tool for use with the T-PLIF implant.
Figure 13B:
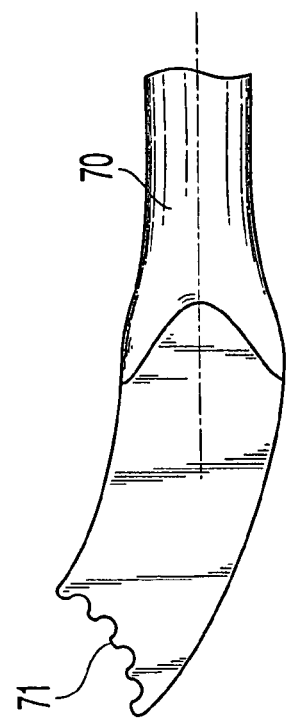
FIG. 13B is a close-up view of the tip of the impactor tool shown in FIG. 13A.
Figure 14:
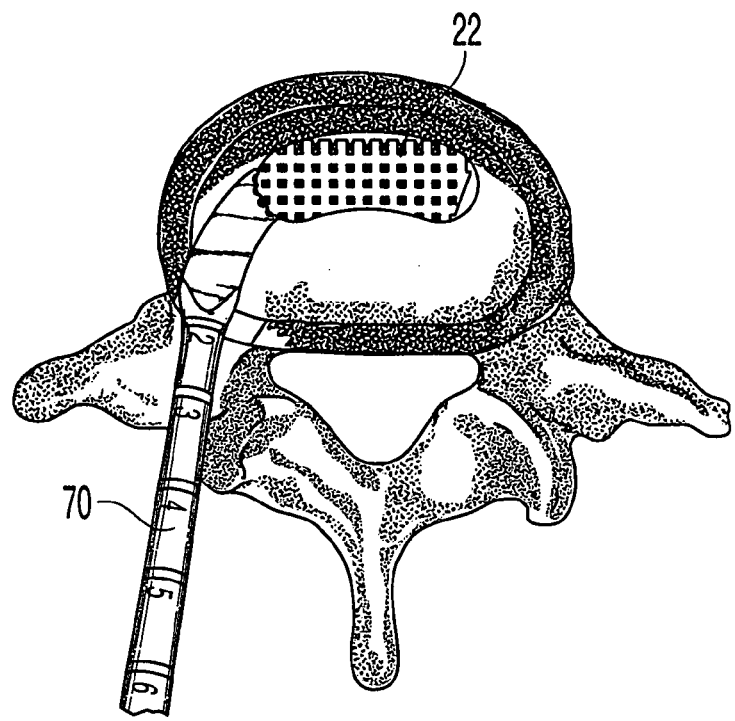
FIG. 14 is a top view of a typical human vertebrae showing an implant according to the present invention being properly positioned into an affected disc space using the impactor tool shown in FIG. 13A.
Figure 15:
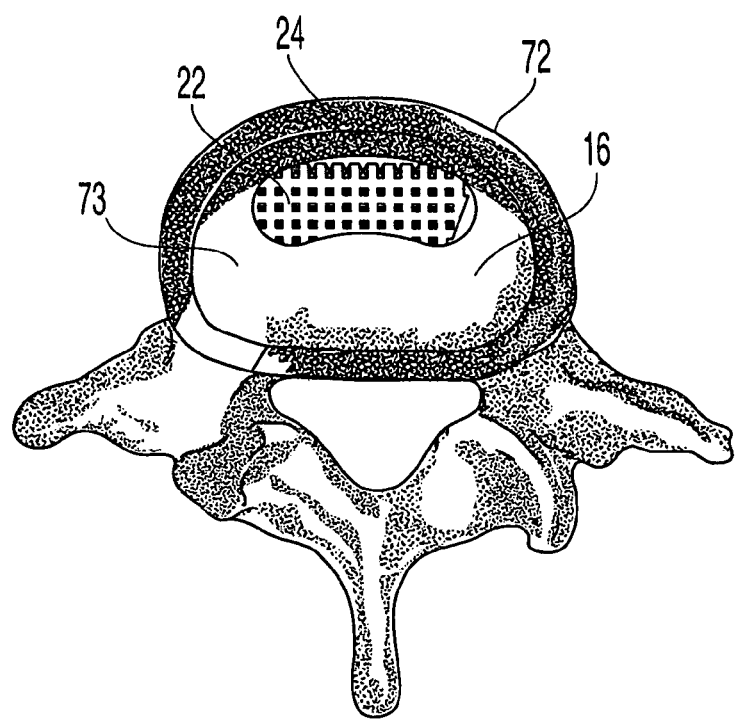
FIG. 15 is a top view of the vertebrae of FIG. 1 showing the T-PLIF implant in a final position.

Upon identifying and removing the best fitting trial spacer, a T-PLIF implant of appropriate size is selected. At this time, prior to placement of the T-PLIF implant, bone graft material, such as autogenous cancellous bone or a bone substitute, should be placed in the anterior and lateral aspect of the affected disc space. As shown in FIGS. 11C and 11D, T-PLIF implant 22 is then held securely using a surgical instrument such as implant holder 66 (shown more clearly in FIG. 11A), which engages the channels or slots 34 at one end of implant 22. The tips 67 of implant holder 66 may be curved or angled to mate with curved implant 22 and facilitate insertion of implant 22 into disc space 16. T-PLIF implant 22 is then introduced into the intravertebral disc space 16 via the transforaminal window, as shown in FIG. 11D. A guide tool having a curved blade 68 (shown in FIG. 12) to match the curvature of the anterior face of implant 22 may be used to properly guide the implant into affected disc space 16. Slight impaction may be necessary using implant holder 66 (shown in FIG. 11A) or an impactor tool 70 (shown in FIG. 13A) to fully seat the implant. As shown in FIGS. 13A & 13B, impactor tool 70 may also be curved or angled to facilitate seating of the implant through the narrow transforaminal window. Also, the face 71 of impactor 70 may be concavely shaped to mate with the end of implant 22, as shown in FIG. 14. Once the T-PLIF implant is in the desired final position, such as the symmetric final position shown in FIG. 15 or the asymmetric position shown in FIG. 5, implant holder 66, and possibly guide tool 68, is removed and additional bone graft material 73 may be inserted. Preferably, T-PLIF implant 22 should be recessed from the anterior edge 72 of the vertebral body. As shown in FIG. 15, the curvature of anterior face 24 of implant 22 is substantially the same as the curvature of anterior edge 72 of disc space 16. In the symmetric seated position shown in FIG. 15, a single T-PLIF implant 22 provides balanced support to the spinal column about the midline of the spine.

While certain preferred embodiments of the implant have been described and explained, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A method for implanting an intervertebral implant into a disc space of a patient comprising:
   distracting adjacent vertebra;
   removing an inferior facet of the cranial vertebrae and a superior facet of the caudal vertebrae to create a transforaminal window from a posterior side of the patient's spine;
   removing substantially all of the disc material between the adjacent vertebra;
   removing the superficial layers of the vertebra endplates to expose bleeding bone;
   inserting and removing at least one trial fit spacer until a desired implant thickness is determined;
   inserting an implant into the intervertebral disc space via the transforaminal window; and
   guiding the implant through the transforaminal window into a desired position within the disc space
   wherein the implant has a curved, concave posterior face and a curved, convex anterior face, both curved posterior and anterior faces extending along a longitudinal axis of the implant; a pair of convex narrow ends separating the posterior and anterior faces; superior and inferior faces for contacting upper and lower vertebral endplates, the superior and inferior surfaces defining a thickness of the implant; and first and second non-threaded, horizontal channels configured and adapted for engagement by the insertion tool, the first channel disposed along at least a portion of the curved posterior face and the second channel disposed along at least a portion of the curved anterior face; wherein the superior and inferior faces are convex and include a plurality of undulating surfaces thereon.

2. The method of claim 1, wherein the implant is guided through the transforaminal window using a guide tool having a curved blade with a curvature that substantially matches the curvature of the anterior face of the implant.

3. The method of claim 2, wherein the inserting and guiding steps comprise first inserting one of the end faces of the implant into the transforaminal window, rotating the implant so that an anterior face of the implant faces anteriorly and moving the implant around the dura.

4. The method of claim 1, further comprising inserting bone graft material into the disc space.

5. The method of claim 1, further comprising impacting the implant to properly locate the implant in the disc space, wherein a face of the impactor is concave to mate with a convex end of the implant.

6. The method of claim 5, wherein the impactor is angled to facilitate proper positioning of the implant within the disc space.

7. The method of claim 1, further comprising removing the inferior facet of the cranial vertebrae and the superior facet of the caudal vertebrae to create a transforaminal window that is approximately 9.0 mm wide.

8. The method of claim 1, wherein the insertion tool has a pair of tips formed on an end thereof for engaging the pair of channels located on the anterior and posterior faces of the implant.

9. The method of claim 8, wherein the insertion tool is angled to facilitate insertion of the implant via the transforaminal window.

10. The method of claim 1, wherein the implant has an arcuate configuration for facilitating insertion of the implant into a symmetric medial-lateral position about the midline of the spine so that a single implant provides balanced support to the spinal column.

11. The method of claim 1, wherein the first and second channels are curved with the anterior and posterior faces for facilitating the insertion of the implant through the transforaminal window into the disk space.

12. A method for implanting an intervertebral implant into a disc space of a patient comprising:
   distracting adjacent vertebra;
   removing an inferior facet of the cranial vertebrae and a superior facet of the caudal vertebrae to create a transforaminal window from a posterior side of the patient's spine;
   removing substantially all of the disc material between the adjacent vertebra;
   removing the superficial layers of the vertebra endplates to expose bleeding bone;
   inserting and removing at least one trial fit spacer until a desired implant thickness is determined;
   inserting an implant into the intervertebral disc space via the transforaminal window; and
   guiding the implant through the transforaminal window into a desired position within the disc space
   wherein the implant has a curved, concave posterior face and a curved, convex anterior face, both curved posterior and anterior faces extending along a longitudinal axis of the implant; a pair of convex narrow ends separating the posterior and anterior faces; superior and inferior faces for contacting upper and lower vertebral endplates, the superior and inferior surfaces defining a thickness of the implant; and first and second non-threaded, horizontal channels configured and adapted for engagement by an implant insertion tool, the first channel disposed along at least a portion of the curved posterior face and the second channel disposed along at least a portion of the curved anterior face; wherein the implant is formed of a plurality of interconnecting bodies assembled to form a single unit.

13. A method for implanting an intervertebral implant into a disc space of a patient comprising:
distracting a pair of adjacent vertebra using at least one instrument selected from the group consisting of a lamma spreader and a lateral distractor;
removing an inferior facet of a cranial vertebrae and a superior facet of a caudal vertebrae using an osteotome to create a transforaminal window from the posterior side of the spine;
removing substantially all of the disc material between the adjacent vertebra using a curette;
removing the superficial layers of the vertebra endplates using a bone rasp to expose bleeding bone;
inserting a trial fit spacer until a desired implant thickness is determined; and
inserting an implant into the intervertebral disc space via the transforaminal window using an insertion tool
wherein the implant has a curved, concave posterior face and a curved, convex anterior face, both curved posterior and anterior faces extending along a longitudinal axis of the implant; a pair of convex narrow ends separating the posterior and anterior faces; superior and inferior faces for contacting upper and lower vertebral endplates, the superior and inferior surfaces defining a thickness of the implant; and first and second non-threaded, horizontal channels configured and adapted for engagement by the insertion tool, the first channel disposed along at least a portion of the curved posterior face and the second channel disposed along at least a portion of the curved anterior face; wherein the superior and inferior faces are convex and include a plurality of undulating surfaces thereon.

14. The method of claim 13, further comprising inserting bone graft material into the disc space.

15. The method of claim 13, further comprising guiding the implant through the transforaminal window using a guide tool having a curved blade with a curvature that substantially matches the curvature of the anterior face of the implant.

16. The method of claim 15, wherein the inserting and guiding steps comprise first inserting one of the end faces of the implant into the transforaminal window, rotating the implant so that an anterior face of the implant faces anteriorly and moving the implant around the dura.

17. The method of claim 13, further comprising impacting the implant using an impactor to properly locate the implant in the disc space, wherein a face of the impactor is concave to mate with a convex end of the implant.

18. The method of claim 17, wherein the impactor is angled to facilitate proper positioning of the implant within the disc space.

19. The method of claim 13, further comprising removing the inferior facet of the cranial vertebrae and the superior facet of the caudal vertebrae to create a transforaminal window that is approximately 9.0 mm wide.

20. The method of claim 13, wherein the insertion tool has a pair of tips formed on an end thereof for engaging the pair of channels located on the anterior and posterior faces of the implant.

21. The method of claim 20, wherein the insertion tool is angled to facilitate insertion of the implant via the transforaminal window.

22. The method of claim 13, wherein the implant has an arcuate configuration for facilitating insertion of the implant into a symmetric medial-lateral position about the midline of the spine so that a single implant provides balanced support to the spinal column.

23. The method of claim 13, wherein the first and second channels are curved with the anterior and posterior faces for facilitating the insertion of the implant through the transforaminal window into the disk space.

24. A method for implanting an intervertebral implant into a disc space of a patient comprising:
distracting a pair of adjacent vertebra using at least one instrument selected from the group consisting of a lamina spreader and a lateral distractor;
removing an inferior facet of a cranial vertebrae and a superior facet of a caudal vertebrae using an osteotome to create a transforaminal window from the posterior side of the spine;
removing substantially all of the disc material between the adjacent vertebra using a curette;
removing the superficial layers of the vertebra endplates using a bone rasp to expose bleeding bone;
inserting a trial fit spacer until a desired implant thickness is determined; and
inserting an implant into the intervertebral disc space via the transforaminal window using an insertion tool,
wherein the implant has a curved, concave posterior face and a curved, convex anterior face, both curved posterior and anterior faces extending along a longitudinal axis of the implant; a pair of convex narrow ends separating the posterior and anterior faces; superior and inferior faces for contacting upper and lower vertebral endplates, the superior and inferior surfaces defining a thickness of the implant; and first and second non-threaded, horizontal channels configured and adapted for engagement by an implant insertion tool, the first channel disposed along at least a portion of the curved posterior face and the second channel disposed along at least a portion of the curved anterior face; wherein the implant is formed of a plurality of interconnecting bodies assembled to form a single unit.

25. A method for implanting an intervertebral implant into a disc space of a patient around the patient's dura comprising:
creating a transforaminal window from a posterior side of the spine;
inserting bone graft material into the disc space;
providing an implant having a body with curved, substantially parallel posterior and anterior faces separated by two narrow implant ends, superior and inferior faces having a plurality of projections for contacting upper and lower vertebral endplates;
inserting the implant into the affected disc space via the transforaminal window with an insertion tool;
guiding the implant around the dura through the transforaminal window using the insertion tool
wherein the implant has a curved, concave posterior face and a curved, convex anterior face, both curved posterior and anterior faces extending along a longitudinal axis of the implant; a pair of convex narrow ends separating the posterior and anterior faces; superior and inferior faces for contacting upper and lower vertebral endplates, the superior and inferior surfaces defining a thickness of the implant; and first and second non-threaded, horizontal channels configured and adapted for engagement by the insertion tool, the first channel disposed along at least a portion of the curved posterior face and the second channel disposed along at least a portion of the curved anterior face.

26. The method of claim 25, further comprising positioning the implant symmetrically about the midline of the spine.

27. The method of claim 26, wherein the insertion tool is angled to facilitate insertion of the implant via the transforaminal window.

28. The method of claim 25, further comprising impacting the implant with an impactor tool to properly position the implant within the affected disc space.

29. The method of claim 28, wherein the impactor tool is angled to facilitate proper positioning of the implant within the affected disc space.

30. The method of claim of 25, further comprising using a curved guide to assist in locating the implant in the affected disc space behind the dura.

31. The method of claim 25, wherein the inserting and guiding steps comprise first inserting the narrow end of the implant into the transforaminal window, rotating the implant so that the anterior face of the implant faces anteriorly and moving the implant around the dura.

32. The method of claim 25, wherein the implant is formed of a plurality of interconnecting bodies assembled to form a single unit.

* * * * *

UNITED STATES PATENT AND TRADEMARK OFFICE
CERTIFICATE OF CORRECTION

PATENT NO. : 7,226,483 B2
APPLICATION NO. : 10/788015
DATED : June 5, 2007
INVENTOR(S) : David Gerber et al.

It is certified that error appears in the above-identified patent and that said Letters Patent is hereby corrected as shown below:

On the Title Page,
Item (54): "METHOD OF PERFORMING A TRANSFORAMINAL POSTERIOR LUMBER INTERBODY FUSION PROCEDURE", should read --METHOD OF PERFORMING A TRANSFORAMINAL POSTERIOR LUMBAR INTERBODY FUSION PROCEDURE--

Column 9, lines 6-7, "lam ma" should read --lamina--

Signed and Sealed this

Twenty-first Day of October, 2008

JON W. DUDAS
*Director of the United States Patent and Trademark Office*

UNITED STATES PATENT AND TRADEMARK OFFICE
CERTIFICATE OF CORRECTION

PATENT NO.        : 7,226,483 B2                           Page 1 of 1
APPLICATION NO. : 10/788015
DATED             : June 5, 2007
INVENTOR(S)       : David Gerber et al.

It is certified that error appears in the above-identified patent and that said Letters Patent is hereby corrected as shown below:

On the Title Page,
Item (54) and Column 1, lines 1-3: "METHOD OF PERFORMING A TRANSFORAMINAL POSTERIOR LUMBER INTERBODY FUSION PROCEDURE", should read --METHOD OF PERFORMING A TRANSFORAMINAL POSTERIOR LUMBAR INTERBODY FUSION PROCEDURE--

Column 9, lines 6-7, "lam ma" should read --lamina--

This certificate supersedes the Certificate of Correction issued October 21, 2008.

Signed and Sealed this

Eleventh Day of November, 2008

JON W. DUDAS
*Director of the United States Patent and Trademark Office*